United States Patent [19]

Nanjo

[11] Patent Number: 5,757,462
[45] Date of Patent: May 26, 1998

[54] OPHTHALMIC APPARATUS FOR PHOTOGRAPHING A SECTION OF AN ANTERIOR PART OF AN EYE

[75] Inventor: Tsuguo Nanjo, Toyohashi, Japan

[73] Assignee: Nidek Company, Ltd., Japan

[21] Appl. No.: 850,291

[22] Filed: May 5, 1997

[30] Foreign Application Priority Data

May 31, 1996 [JP] Japan ................... 8-161076

[51] Int. Cl.[6] ........................... A61B 3/14; A61B 3/10
[52] U.S. Cl. ..................... 351/206; 351/211; 351/221
[58] Field of Search ........................... 351/206, 208, 351/205, 211, 214, 221, 246, 200; 354/62

[56] References Cited

U.S. PATENT DOCUMENTS

| | | | |
|---|---|---|---|
| 5,202,708 | 4/1993 | Sasaki et al. | 351/206 |
| 5,347,331 | 9/1994 | Isogai et al. | 354/62 |
| 5,381,194 | 1/1995 | Nishio et al. | 351/208 |
| 5,436,679 | 7/1995 | Ohtsuka et al. | 351/206 |

FOREIGN PATENT DOCUMENTS 63-297434  8/1988  Japan.

*Primary Examiner*—Hung X. Dang
*Attorney, Agent, or Firm*—Rossi & Associates

[57] ABSTRACT

An ophthalmic apparatus for photographing a section of an anterior part of an eye having slit light projection optical system for projecting a slit light onto an anterior part of an eye to be examined, and section photographing device for photographing a sectional image of the anterior part of the eye where is cut optically by the slit light, including section photographing optical system which is disposed based on the Scheimpflug's principle, the apparatus providing first target projection optical system for projecting a first alignment target onto a cornea of the examined eye, front photographing device for photographing a first alignment target image projected onto the cornea of the examined eye from the front side, first displaying device for displaying an image which is photographed by the front photographing device, second target projection optical system for projecting a second alignment target from a slanting direction corresponding to the examined eye, and second displaying device for displaying a second alignment target image which is photographed by said section photographing device, thereby the propriety of alignment may being judged by observing the displaying condition of the first and second alignment target images respectively on the first and second display device.

9 Claims, 6 Drawing Sheets

OPHTHALMIC APPARATUS FOR PHOTOGRAPHING A SECTION OF AN ANTERIOR PART OF AN EYE

BACKGROUND OF THE INVENTION

1. Field of the Invention

The present invention relates to an ophthalmic apparatus for photographing a section of an anterior part of an eye on the basis of Scheimpflug's principle, and more particularly relates to an ophthalmic apparatus providing an alignment mechanism suitable for specifying a corneal position in order to achieve photomacrography partially.

2. Description of Related Art

In case that an eyeball is cut optically by a slit illumination light so as to obtain a sectional image of the anterior part of the eye by a photographing optical system having an optical axis which slopes corresponding to an optical axis of a slit illumination system, it is conventionally well-known an apparatus for photographing a section of an anterior part of the eye enables to photograph from the front side of cornea through the rear side of crystalline lens based on Scheimpflug's principle of which an arrangement of an optical system is disposed at a position where a cross line which the extension of optical section by the slit illumination light intersects the extension of image section of imaging optical system intersects on the extension of line of a principal plane of photographic lens. In the photography based on this Scheimpflug's principle, since there are enough focal depth in the whole image, the photography can be achieved clearly throughout some such small detail parts.

It is necessary for this sort of apparatus to provide an alignment adjustment for the eye to be examined and the photographing optical system when the photography is performed. Therefore, the present applicant proposed an apparatus providing smooth alignment adjustment as shown in Japanese Laid-open No. SHO63-197434 and so on. The apparatus described in this reference publication provides that an alignment target is projected from the front side of the eye to be examined, the projected target image and the anterior part image are photographed by the photographing optical system from the front, and then they are displayed on display, thereby the alignment is performed by observing the imaging condition of the target image from the front side. The apparatus is further provides a reticle forming device for forming a reticle for the alignment on the display. The upper-lower and left-right alignment is performed so as to achieve the predetermined position related to the reticle image and the target image, and the alignment for forward/backward is performed so as to bring the target image into the best focus.

Meanwhile recently, PRK (Photorefractive Keratectomy) operation has been noticeable as an operation method that the surface of cornea is ablated by use of an excimer laser beam, and then the ametropia of eyeball is corrected by changing corneal curvature. In this sort of operation, it is necessary to confirm the incidence of haze (corneal epithelium opacification), condition of convergent heal or the like after the operation. Furthermore, the investigation by analyzing a corneal shape after PRK operations needs the examination of the efficacy of medical treatment and the prevention against the incidence of haze, moreover needs the knowledge of the corneal shape which is removed and corrected. In order to know a condition of cornea after this sort of operation, it is very effective to use the sectional image of cornea obtained by the above mentioned apparatus for photographing a section of the anterior part of the eye.

However, although the above-mentioned alignment mechanism has sufficient accuracy by the standard photography for the whole anterior part of the eye including from the front side of cornea to the rear side of crystalline lens, in case of a purpose for the photomacrographing a part of section of the cornea like the above-described, it resulted in disadvantage that alignment accuracy of working distance only by focusing the alignment target was not always sufficient, also the sectional image of cornea could not be necessary obtained at the predetermined position. Also, the focusing of target image from the front side depends upon each individual different level of operators.

SUMMARY OF THE INVENTION

The present invention has been made in view of the above circumstances and has an object the above problems and to provide an ophthalmic apparatus for photographing a section of an anterior part of an eye, capable of alignment accurately and simply for photomacrography of corneal section.

Additional objects and advantages of the invention will be set forth in part in the description which follows and in part will be obvious from the description, or may be learned by practice of the invention. The objects and advantage of the invention may be realized and attained by means of the instrumentalities and combinations particularly pointed out in the appended claims.

To achieve the objects and in accordance with the purpose of the invention, as embodied and broadly described herein, an ophthalmic apparatus for photographing a section of an anterior part of an eye of this invention which having slit light projection optical system for projecting a slit light onto an anterior part of an eye to be examined, and section photographing means for photographing a sectional image of the anterior part of the eye where is cut optically by the slit light, including section photographing optical system which is disposed based on the Scheimpflug's principle, comprises first target projection optical system for projecting a first alignment target onto a cornea of the eye to be examined, front photographing means for photographing a first alignment target image projected onto the cornea of the eye to be examined from the front side, first displaying means for displaying an image which is photographed by the front photographing means, second target projection optical system for projecting a second alignment target from a slanting direction corresponding to the eye to be examined, and second displaying means for displaying a second alignment target image which is photographed by said section photographing means, thereby the propriety of alignment may be judged by observing the displaying condition of the first and second alignment target images respectively on the first and second displaying means.

As described above, according to the present invention, even though a section of the anterior part of the eye is photomacrographed, the apparatus enables to exclude an alignment error by operator and enables to perform alignment simply and accurately.

Additionally, the apparatus enables to improve a reproductivity of the photomacrography of the section so as to obtain a reliable image data on such a condition of analyzing change by time process and the like.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

In the drawings.

DETAILED DESCRIPTION OF THE PREFERRED EMBODIMENTS

<The first preferred embodiments>

Figure 1A:
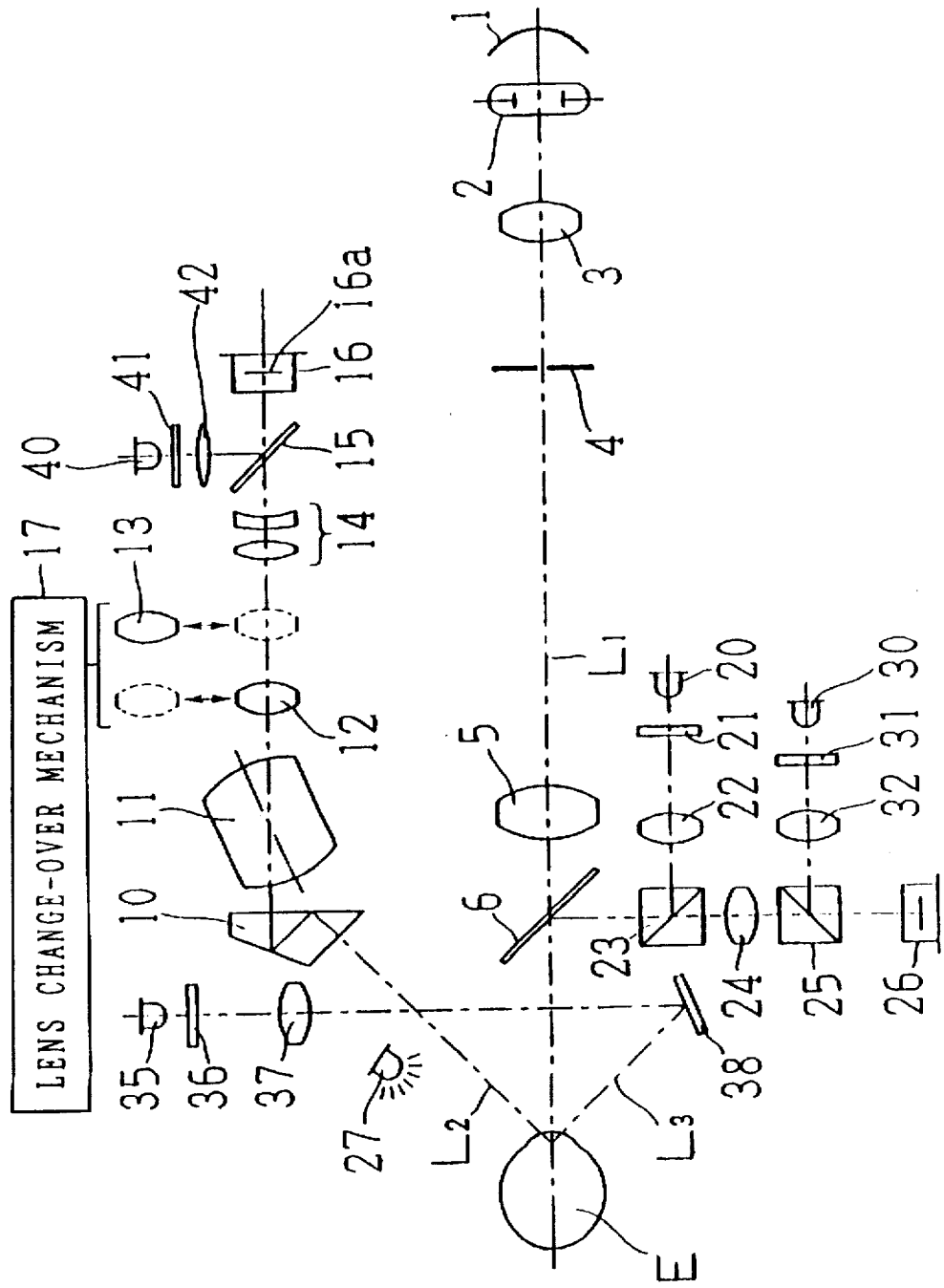
FIG. 1A is a view showing an arrangement of optical systems of the ophthalmic photographing apparatus of the first preferred embodiment of the present invention.

A detailed description of one preferred embodiment of an ophthalmic apparatus for photographing a sectional image of the anterior part of the eye embodying the present invention will now be given referring to the accompanying drawings. FIG. 1A is a view showing an arrangement of optical systems of the apparatus of the first preferred embodiment.

(Slit light projection optical system)

Reference numeral 1 denotes a reflecting mirror, 2 is a flash lamp for photography, 3 is a condenser lens, 4 is a slit aperture diaphragm, 5 is a projection lens, and 6 is a dichroic mirror which is disposed slantingly on an optical axis $L_1$ of the slit light projection optical system. The dichroic mirror 6 has a characteristics of transmitting most of visible light and reflecting infrared-ray.

Luminous flux emitted from the photographing flash lamp 2 is collected by the condenser lens 3, thereby the slit aperture diaphragm 4 is illuminated.

The luminous flux which is formed to be a slender slit-shape by the slit aperture diaphragm 4 is transmitted through the dichroic mirror 6 by the projection lens 5, then it is projected onto the eye E to be examined, thereby a slit-image of the slit aperture diaphragm 4 is projected onto the anterior part of the eye E to be examined. By this process, optic media of the anterior part of the eye to be examined (such as cornea and crystalline lens) are illuminated under the condition of being cut optically by a white light source within a range of visible level. Incidentally, since photography is performed by use of scattering light from biomolecule of cornea and crystalline lens of the eye to be examined which are cut optically, if the wavelength becomes shorter, the scatter may be greater as well as a capacity for detecting may increase. However, it may be preferred to use a moderate white light source, because an optical toxicity would be more harmful to eyeball within a range of ultraviolet level.

(Slit-section photographing optical system)

Reference numeral $L_2$ denotes a photographic optical axis of slit-section photographing optical system. Reference numeral 10 denotes a deviation angle prism for changing a direction of the photographic optical axis $L_2$. Reference numeral 11 is a photographic lens, 12 is an image-forming lens for use in photomacrography, 13 is an image-forming lens for use in standard photography, 14 is an anamorphic lens, 15 is a beam splitter, and 16 is a CCD camera.

Figure 1B:
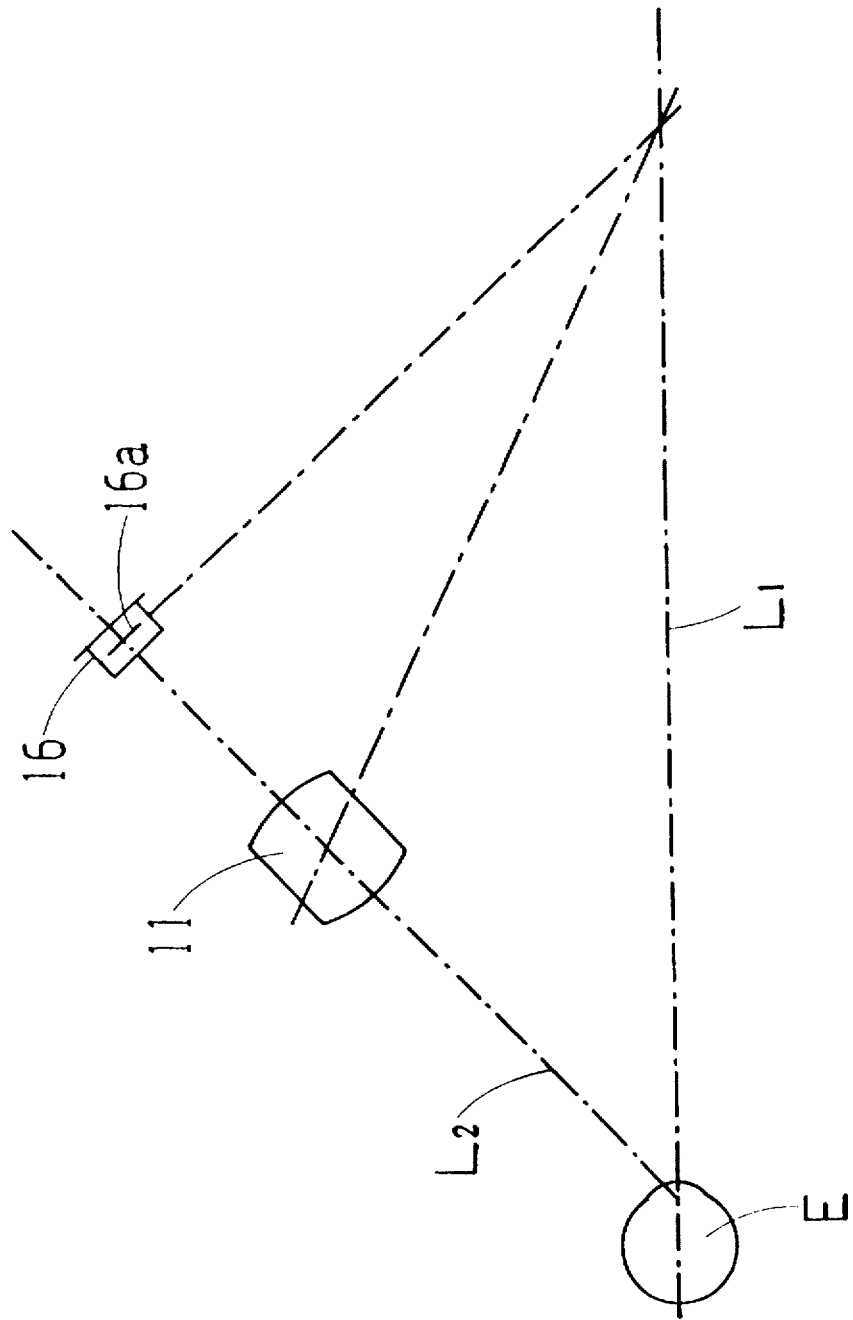
FIG. 1B is a view showing an optical arrangement based on Scheimpflug's principle of the apparatus.

The photographic optical axis $L_2$ is disposed so as to intersect with holding an inclination angle of 45° corresponding to the optical axis $L_1$ at adjacent to a position of interocular side of half distance of the radius of corneal curvature, when an alignment is almost completed by observing from the front side. The photographic lens 11 is disposed slantingly corresponding to the photographic optical axis of which the direction can be changed by the deviation angle prism 10 so as to fulfill Scheimpflug's principle. That is, when the deviation angle prism 10 is not utilized, a cross line which the extension of optical section of the anterior part of the eye to be examined by the slit illumination light intersects the extension of a imaging plane 16a of the CCD camera 16 is arranged so as to intersect the extension of a principal plane of the photographic lens 11 (see FIG. 1B). According to this optical arrangement, a sectional image photographed by the CCD camera 16 (a slit-light optical cutting sectional image which is formed by the scattering light from biomolecule of an anterior part of the eye at the center of collective point of slit-light) can hold a focal depth for focusing the approximate entirety of its sectional image.

The image-forming 12 lens for use in photomacrography and the image-forming lens 13 for use in standard photography can be changed over selectively on an optical axis by a lens change-over mechanism 17. In case of photographing from the front side of cornea through the rear side of crystalline lens, the image-forming 13 lens for use in standard photography is utilized, and in case of photomacrographing a part of section of cornea or crystalline lens or the like, the image-forming 12 lens for use in photomacrography is utilized.

Besides, the anamorphic lens 14 is an optical element to correct a distorted image photographed from a slanting direction (a direction of angle of 45°), and normally the anamorphic lens 14 consists of a combination with a cylindrical lens.

(First alignment target projection optical system)

Reference numeral 20 denotes a light source for the first alignment for projecting an alignment target from the front side of an eye to be examined (a direction of visual axis), and emitting an infrared-ray including a part of visible light for sharing with a fixation light source. Reference numeral 21 denotes a target plate having a pin-hole aperture on a projection optical axis, 22 is a projection lens, thereby the target plate 21 is positioned at adjacent to the front focusing distance of the projection lens 22. Reference numeral 23 denotes a beam splitter.

The target plate 21 is illuminated by a light emitted from the light source 20. An alignment light emerged from the target plate 21 reflects at the beam splitter 23 after the alignment light is formed to a parallel luminous flux by the projection lens 22. Thereafter, the alignment light is reflected by the dichroic mirror 6, then is forwarded to the eye E along the optical axis $L_1$, so that an target image of the target plate 21 is formed by surface reflection of cornea at the position of interocular side of half distance of the radius of corneal curvature.

Additionally, since the light source 20 includes a part of visible light, the first alignment target projection optical system combines a fixation optical system, thereby a fixation target by the pin-hole aperture of the target plate 21 is fixated onto the eye to be examined.

(Front photographing optical system for an anterior part of an eye)

Reference numeral 24 denotes a photographic lens, 25 is a beam splitter, and 26 is a CCD camera for observing the front side with having a sensitivity within an infrared level. Reference numeral 27 is an infrared-illumination light source for illuminating the anterior part of the eye.

A partial luminous flux reflected at a cornea among alignment luminous flux which is projected by the first alignment target projection optical system is photographed by the CCD camera 26, after reflected at the dichroic mirror 6, passed through the beam splitter 23, the photographic lens 24 and the beam splitter 25. Also, the anterior part image of the eye E to be examined illuminated by the illumination light source 27, after passed though the same optical path, is photographed by the CCD camera.

(Front reticle optical system)

Reference numeral 30 denotes illumination light for a reticle-plate source, and 31 is a reticle plate that an aiming mark is formed. Although the aiming mark used in the preferred embodiment is a circular shape at the center of the optical axis, any shapes of aiming mark may be acceptable in order to achieve such as a simple aiming. Reference numeral 32 denotes a reticle projection lens. The aiming mark of the reticle plate 31 illuminated by the illumination light source for a reticle-plate 30, after passed through the reticle projection lens 32, is reflected at the beam splitter 25, thereby the aiming mark as well as the anterior eye image and target images are photographed by the CCD camera 26.

(Second alignment target projection optical system)

Reference numeral 35 denotes a light source for the second alignment such as a light emitting diode (LED) and the like (a visible light may be utilized as an alignment light, also a laser diode and the like may be used occasionally), 36 is a target plate having a pin-hole aperture at the center of optical axis, 37 is a projection lens, and 38 is a mirror.

A projection optical axis $L_3$ of the second alignment target projection optical system is disposed within an identical plate to the optical axis $L_2$, and is also arranged symmetrically with respect to the optical axis $L_2$ so as to put the optical axis $L_1$ between $L_2$ and $L_3$ with having an inclination angle of 45°. The target plate 36 is illuminated by a light emitted from the light source 35, a target luminous flux by the target plate 36 reflects at the mirror 38, thereby the target luminous flux is collected and projected onto the eye E to be examined from the slanting direction.

(Reticle optical system for photographing a section)

Reference numeral 40 denotes a illumination light source for a reticle-plate, 41 is a reticle plate having a aiming mark for alignment (for instance, a grid mark), and 42 is a projection lens. A aiming mark illumination flux emerged from the reticle plate 41 is photographed by the CCD camera 16 passed through the projection lens 42 and the beam splitter 15, and then it is displayed in a display 55 which mentioned below.

In the above-mentioned optical systems, since the slit-section photographing optical system, the second alignment target projection optical system, the reticle optical system for photographing a section and the slit aperture diaphragm 4 are structured so as to rotate the optical axis $L_1$ by rotation mechanism not illustrated in this specification, a section of optional angle can be photographed.

Figure 2:
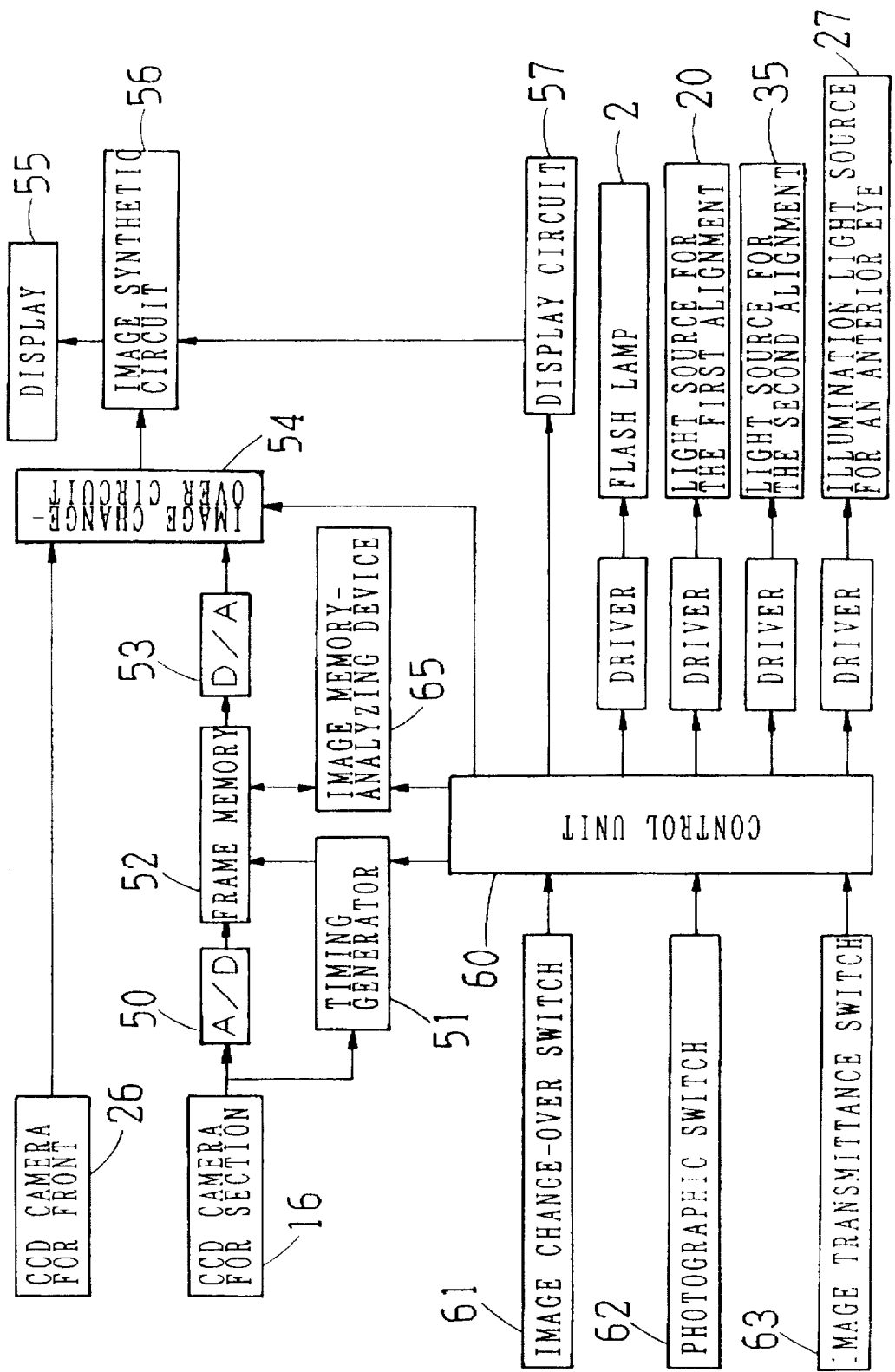
FIG. 2 is a block diagram of an important part showing a control system of the apparatus of the first preferred embodiment.

FIG. 2 is a block diagram of an important part showing a control system of the apparatus of the preferred embodiment.

A video signal from the CCD camera 16 is digitized by an A/D converter circuit 50, and the video signal is inputted into a frame memory 52 with synchronizing to a signal of a timing generator 51. The image signal inputted into the frame memory 52 is transmitted to an image change-over circuit 54 after the image signal is transformed to the video signal passed through a D/A converter circuit 53. The image change-over circuit 54 receives a command signal from a control unit 60 based on an operation of an image change-over switch 61, then a state of displayed-image of the display 55 is changed over to a photo-image by the CCD camera 26 and a photo-image by the CCD camera 16.

Reference numeral 56 denotes a image synthetic circuit for synthesizing various information display generated by a display circuit 57 and both images of the CCD cameras 26 and 16 and then displaying on the display 55. By the image synthetic circuit 56 and display circuit 57, the reticle image for photographing a section and the front reticle image of the above-mentioned optical systems may be synthesized electrically and displayed on the display 55.

Furthermore, a sectional image of anterior eye freeze-memorized by the frame memory 52 is transmitted to an image memory-analyzing device 65 inputted by operating an image transmittance switch 63.

Next, it will be described hereinafter as regards the operation for the above-mentioned structured apparatus.

(A) Standard photographing of section

Figure 3:
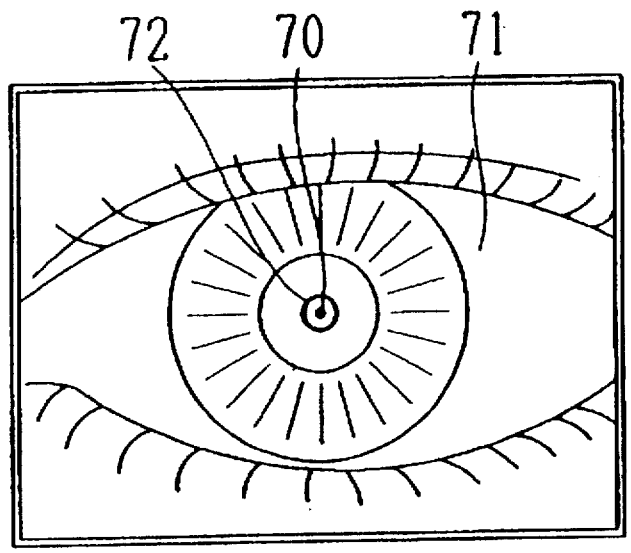
FIG. 3 is a view showing a display sample of a front image photographed by front photographing optical system for an anterior part of the eye.

In case of photographing section including from the front side of cornea through the rear side of crystalline lens, by operating the lens change-over mechanism, the image-forming lens 13 for standard photography is disposed on the optical axis of the slit-section photographing optical system. After the eye to be examined is positioned at a predetermined position, an target of the target plate 21 which is illuminated by the first alignment light source 20 is projected onto a cornea of the eye to be examined. Since the first alignment target projection optical system is shared with the fixation optical system, the target of the target plate 21 is fixated onto the eye to be examined. A front image which is photographed by the CCD camera 26 of the front photographing optical system for an anterior eye is transmitted to the display 55 passed through the image change-over circuit 54. On the display 55, as shown in FIG. 3, an anterior part image 71 of the eye to be examined and a reticle image 72 as well as an target of the first alignment 70 are displayed.

While the operator observes this front image, the operator shifts the apparatus upper-lower and left-right with respect to the eye to be examined by operating a joystick not shown or the like so that the target image 70 is positioned at the center of the reticle image 72. By this process, an optical axis arrangement between the apparatus and the eye E to be examined can be completed. Furthermore, by shifting the apparatus forward and backward so as to make the target image 70 be a smallest and clear image, the operator starts an alignment of working distance. As a result of this, in photography of the whole of the anterior part of eye including from the front side of cornea through the rear side of crystalline lens, the alignment can be completed with keeping approximately sufficient accuracy.

Figure 4:
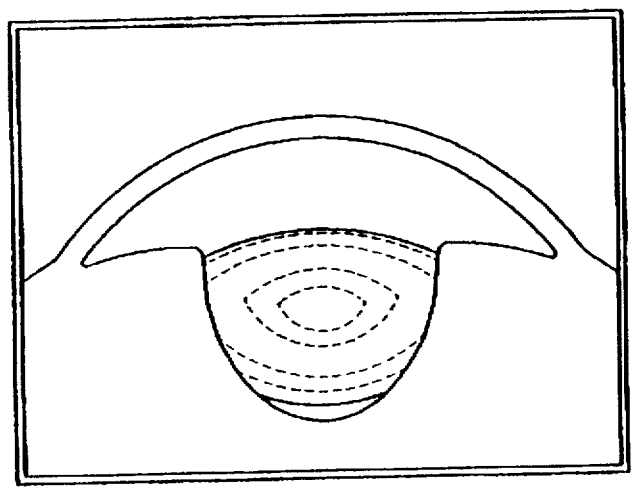
FIG. 4 is a view showing a display sample of a sectional image of an anterior part of the eye by standard photography for section.

When the alignment is completed by observing the front image, the photography of a sectional image is performed by pressing a photographic switch 62. The control unit 60 controls so that the flash lamp 2 is emitted by an input signal of the photographic switch 62, then a slit light is projected on the anterior part of the eye to be examined. The sectional image of the cornea and crystalline lens which are cut optically by the slit illumination light is photographed by the CCD camera 16 of the slit-section photographing optical system. By the control unit 60, this photo-image is frozen into the frame memory 52 passed through the timing generator 51. On the display 55, as shown in FIG. 4, the sectional image of the anterior part from the front side of cornea through the rear side of crystalline lens is displayed so as to approximately center an interocular position of half distance of the radius of corneal curvature that the first alignment target image is formed.

(B) Photomacrographing of section

In case of photomacrographing section, the image-forming lens 12 for use of photomacrography is substituted for the image-forming lens 13 for use of standard photography, thereby the image-forming lens 12 is changed over and disposed on the optical axis of the slit-section photographing optical system. Next, the target image by the first alignment light source 20 is projected onto the eye to be examined, as the same process of the standard photographing of section, with observing the front image (referring to FIG. 3) displayed on the display 55, the upper-lower and left-right alignment is performed so that the target image 70 is positioned in the center of the reticle image 72, then the approximate alignment of working distance is performed so as to make the target image 70 be a smallest and clear image.

In the photography of the comparative wide range such as from the front side of cornea through the rear side of crystalline lens, although the sufficient alignment is completed approximately, for instance, in case of photomacrographing a part of section of cornea, it may result in disadvantages that the accuracy of focusing the target image on the display screen photographed by the front side may be limited, therefore some dispersion may be caused during the alignment of working distance. The extent of this dispersion may be influenced by each individual different level of operators.

Furthermore, since the apparatus of the preferred embodiment is suitable for photographing the section of the whole of anterior part of eye including from the front side of cornea through the rear side of crystalline lens, the photographic optical axis $L_2$ is disposed so as to intersect the optical axis $L_1$ at a position (the interocular position of half distance of the radius of corneal curvature) where the first alignment target image is formed. Thus, in order to photograph on a part of cornea as a basis, it is necessary to shift the apparatus slightly (approximately 3mm) backward corresponding to the eye to be examined, also the photographing position may fail to be arranged and stable.

As described above, if the section of cornea is photographed based on propriety judgment of alignment only by observing the front image, the photo-image may be photographed under a condition of being displaced with respect to a desired position because the photographing of section is performed from the slanting or side direction (angle of 45°) corresponding to the eye to be examined. Unless the corneal section is constantly obtained at an desired position, reliability of analyzed data may be effected in case of making a comparison of analyzing image and the like later. For instance, in case of the sectional images of cornea which is photographed both ahead and behind of the direction of the slit light projection optical axis, any displacement of a projecting distance of slit light projection or slit-section photographic optical axis may be caused, therefore even though the photography is performed with the same quantity of flash light, its photo-image may have some different quantity of light effectively. This is, especially in case that the extent of corneal inflammation is examined based on the density data of photo-image, its reliability may not be obtained.

Accordingly, the present apparatus provides that after the propriety judgment of alignment is completed by the front photo-image, more detail alignment of working distance is performed by use of the slanting side photo-image of the eye to be examined by the silt-section photographing optical system. The operator presses the image change-over switch 61 after completing the optical axis arrangement and the approximate alignment of working distance by observing the front image by following the above-mentioned process. The control unit 60 controls the image change-over circuit 54 based on the command signal, thereby the display image of the display 55 is changed over to the photo-image by the CCD camera 16. Also, the control unit 60 controls that the light source 27 for illuminating an anterior eye is turned off and the light source 35 for the second alignment is turned up. When the second alignment target is projected onto the cornea of the eye to be examined by lighting up the light source 35, and the target luminous flux reflected near the vertex of cornea is caught by the CCD camera 16, the target image is displayed on the display 55 of which display is changed over (when the target is not appear, the apparatus is shifted slightly backward, thereby the second alignment target luminous flux reflects at the vertex of cornea so as to go into the optical path of the slit-section photographing optical system, and then the target image is caught by the CCD camera 16 and appears on the display 55). In addition, the aiming mark by the reticle optical system for photographing a section is photographed in the CCD camera 16, and displayed on the display 55.

Figure 5:
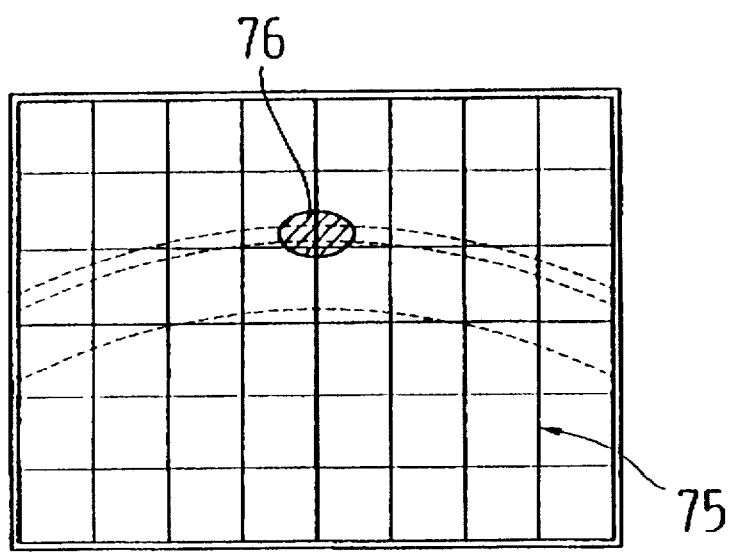
FIG. 5 is a view showing a display sample of image which is photographed by a slit section photographing optical system upon performing alignment.

FIG. 5 is a view showing a display sample at this time, thereon a grid aiming mark 75 and the second alignment target image 76 are displayed. The operator judges the propriety of alignment by observing this display. For instance, the detail alignment arrangement is carried out by shifting the apparatus forward-backward so as to position the target image 76 in the center of the grid aiming mark image 75. Or as another way, on the basis of the target image 76 equivalent to a vertex position of cornea, the detail alignment arrangement is performed at the photographic position of an optional corneal section according to the positional relation with the grid aiming mark image 75.

When the alignment is completed by observing the target image 76, the photographic switch 62 is pressed so as to emit the flash lamp 2. The corneal section which is cut optically by the slit illumination light is photographed by the CCD camera 16, then the image frozen by the frame memory 52 is displayed in the display 55. The image frozen by the frame memory 52 is transmitted to the image memory-analyzing device 65 by pressing the image transmittance switch 63 and used for analysis in order to know a corneal shape or the like.

Beside, in the photomacrographing of a section of anterior part of the eye, the grid aiming mark 75 and the target image 76 may be photographed simultaneously, or the light source 35 for the second alignment and the illumination light source for a reticle-plate 40 may be turned off with synchronizing to the input signal of the photographic switch 62, if they are unnecessary.

As described in the above, upon the photomacrographing of a section of anterior part of the eye, the projected target image from the slanting direction of the eye to be examined is caught at the slit-section photographing optical system, and by observing this, the high accurate alignment can be simply performed. Furthermore, the reproductivity of the slit sectional image based on the vertex of cornea can be improved, and in case of examining and analyzing the corneal shape after PRK operation, the comparison of exact data in its change by time process can be obtained.

<The second preferred embodiment>

Figure 6:
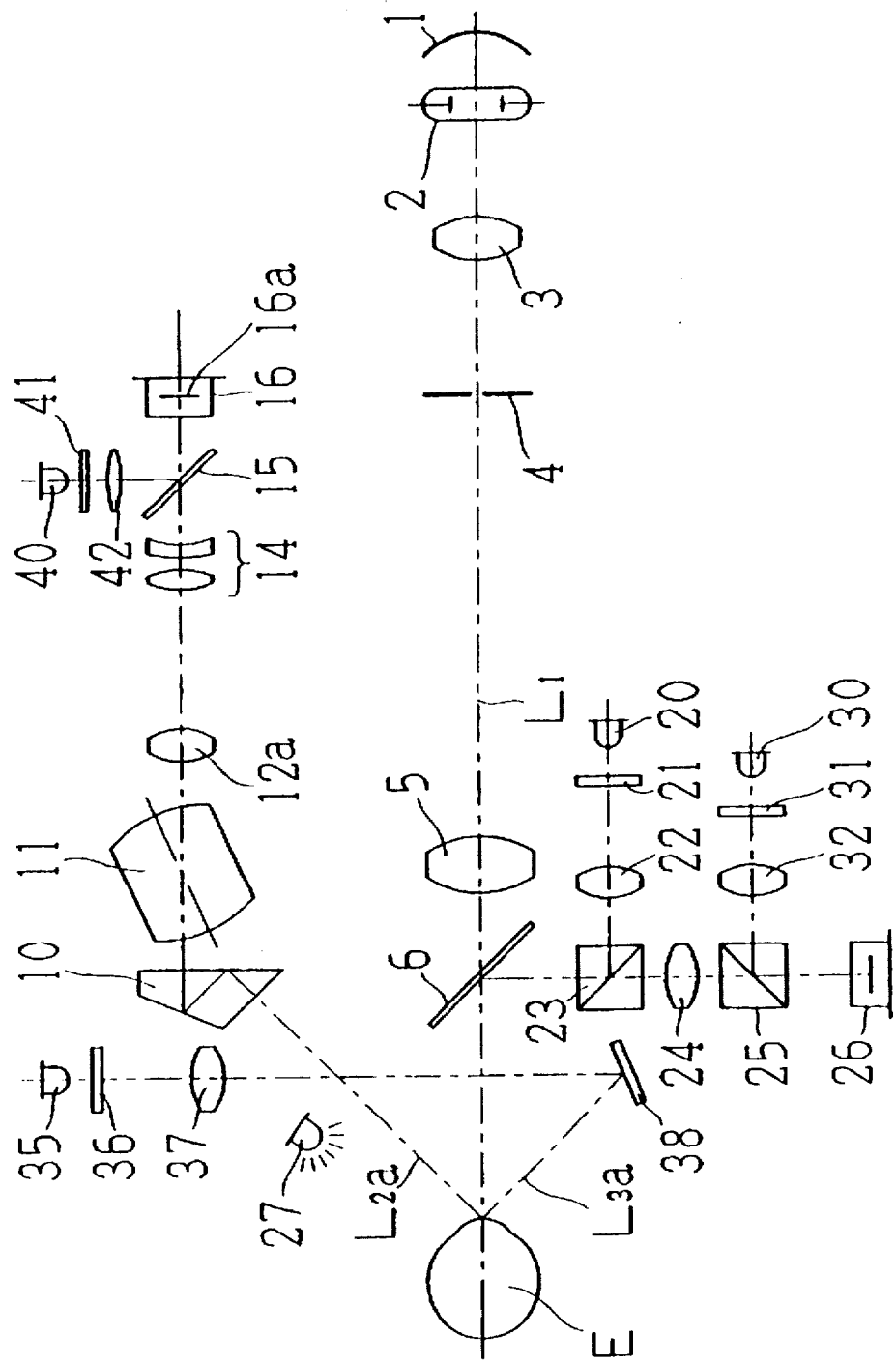
FIG. 6 is a view showing an arrangement of optical systems of the ophthalmic photographing apparatus of the second preferred embodiment of the present invention.

FIG. 6 is a view showing an arrangement of an optical system of the apparatus of the second preferred embodiment.

The same mark numbers in FIG. 6 are attached to the same parts in the first preferred embodiment.

Reference numeral 12a of the slit-section photographing optical system denotes an image-forming lens for photomacrography, which is fixed and disposed on the photographic optical axis. Also, a photographic optical axis $L_2a$ and a projection optical axis $L_3a$ of the second alignment target projection optical system are disposed so that each optical axis $L_2a$ and $L_3a$ intersects the optical axis $L_1$ at adjacent to the vertex of cornea, which makes symmetrically each inclination angle have 45°, when the alignment is completed by observing the front image.

The apparatus of the first preferred embodiment provides that in order to achieve a structure that a photographic magnification can be varied so as to make standard photographing for section and photomacrographing for section possible, when the alignment has been completed by observing the front image, the optical arrangement is based upon the standard photography that the photographic optical axis $L_2$ and the projection optical axis $L_3$ of the second alignment target intersect the optical axis $L_1$ at adjacent to the interocular position of half distance of the radius of corneal curvature. Therefore, upon photomacrographing, after the alignment by observing the front image, it is necessary to take process such as the second alignment target image which reflects at the vertex of cornea is positioned in the center of the display screen by shifting the apparatus backward slightly.

In contrast, since the above-mentioned optical arrangement is set in the apparatus of the second preferred embodiment, after the alignment is completed by observing the front image, when the image is changed over to the image by the CCD camera 16, without shifting the apparatus, the second alignment target image can appear surrounding the center of the display screen, therefore the alignment arrangement of working distance can be achieved easily on the basis of the vertex of cornea.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for photographing a section of an anterior part of an eye having slit light projection optical system for projecting a slit light onto an anterior part of an eye to be examined, and section photographing means for photographing a sectional image of the anterior part of the eye where is cut optically by said slit light, including section photographing optical system which is disposed based on the Scheimpflug's principle, comprising:

first target projection optical system for projecting a first alignment target onto a cornea of the eye to be examined;

front photographing means for photographing a first alignment target image projected onto the cornea of the eye to be examined from the front side;

first displaying means for displaying an image which is photographed by said front photographing means;

second target projection optical system for projecting a second alignment target from a slanting direction corresponding to the eye to be examined; and second displaying means for displaying a second alignment target image which is photographed by said section photographing means, thereby the propriety of alignment may being judged by observing the displaying condition of the first and second alignment target images respectively on the first and second displaying means.

2. An ophthalmic apparatus according to claim 1, further comprising first aiming mark forming means for forming an aiming mark in order to judge the propriety of alignment by said first alignment target image which is projected onto the cornea of the eye to be examined.

3. An ophthalmic apparatus according to claim 1, further comprising second aiming mark forming means for forming an aiming mark in order to judge the propriety of alignment by said second alignment target image which is projected onto the cornea of the eye to be examined.

4. An ophthalmic apparatus according to claim 1, wherein an optical axis of said slit light projection optical system is put between a projection optical axis of said second target projection optical system and a photographic optical axis of said section photographing optical axis, also the projection optical axis of said second target projection optical system is disposed symmetrically with respect to a photographic optical axis of said section photographing optical axis.

5. An ophthalmic apparatus according to claim 1, wherein said first and second displaying means are shared, and have image change-over means for changing over images which are photographed by said section photographing means and said front photographing means.

6. An ophthalmic apparatus according to claim 1, including magnification changing means for changing the magnification of image which is photographed by said section photographing means.

7. An ophthalmic apparatus according to claim 6, wherein said magnification changing means comprises image forming lenses with various magnifications which are changed over and disposed selectively on the optical path in said section photographing optical system.

8. An ophthalmic apparatus according to claim 7, wherein said image forming lenses with various magnifications have a first lens for enabling the photography of a section of the anterior part including from the front side of cornea through the rear side of crystalline lens, and a second lens for enabling the photomacrography of a section of a part of the cornea.

9. An ophthalmic apparatus according to claim 1, wherein the photographic optical axis of said section photographing optical system and the projection optical axis of said second target projection optical system are disposed so as to intersect each axis near the vertex of cornea of the eye to be examined; when the alignment is completed by observing said first alignment target image.

* * * * *

UNITED STATES PATENT AND TRADEMARK OFFICE
CERTIFICATE OF CORRECTION

PATENT NO. : 5,757,462
DATED : May 26, 1998
INVENTOR(S) : Tsuguo NANJO

It is certified that error appears in the above-indentified patent and that said Letters Patent is hereby corrected as shown below:

On title page, item [56]

In the listing of the references cited:

Delete " 63-297434" and insert -- 63-197434--.

Signed and Sealed this

Eighth Day of September, 1998

Attest:

BRUCE LEHMAN

*Attesting Officer*  Commissioner of Patents and Trademarks